United States Patent [19]

Takemoto et al.

[11] Patent Number: 5,494,823
[45] Date of Patent: Feb. 27, 1996

[54] APPARATUS FOR CULTURING MICROORGANISM

[75] Inventors: Masahiro Takemoto, Kashihara; Hiroshige Yamauchi, Kobe, both of Japan

[73] Assignee: Shimakyu Chemical Co. Ltd., Osaka, Japan

[21] Appl. No.: 284,506

[22] PCT Filed: Oct. 4, 1993

[86] PCT No.: PCT/JP93/01440

§ 371 Date: Aug. 8, 1994

§ 102(e) Date: Aug. 8, 1994

[87] PCT Pub. No.: WO94/09151

PCT Pub. Date: Apr. 28, 1994

[30] Foreign Application Priority Data

Oct. 21, 1992 [JP] Japan ................................. 4-307610

[51] Int. Cl.$^6$ ................................................ C12M 3/04
[52] U.S. Cl. ...................... 435/287.4; 422/56; 422/60; 435/240.23; 435/287.8; 435/305.4; 435/305.1
[58] Field of Search ............................ 422/56, 60; 435/1, 435/240.23, 284, 285

[56] References Cited

U.S. PATENT DOCUMENTS 4,452,887  6/1984  Kitajima et al. ..................... 435/14

FOREIGN PATENT DOCUMENTS

| 0054679 | 10/1981 | European Pat. Off. . |
|---|---|---|
| 2518282 | 10/1975 | Germany . |
| 50-145576 | 11/1975 | Japan . |
| 2-34600 | 8/1990 | Japan . |
| 1502674 | 3/1978 | United Kingdom . |
| 2104215 | 3/1983 | United Kingdom . |
| 8602664 | 9/1986 | WIPO . |

Primary Examiner—David A. Redding
Attorney, Agent, or Firm—Davis, Bujold & Streck

[57] ABSTRACT

The object of the present invention is to permeate sample solution uniformly into an absorbent fibrous sheet. The gelation agent soluble in cold water absorbs moisture and forms a gel, thereby forming a gel medium. Microorganisms are thus cultivated. The surface of a waterproof plate 2 is coated with the mixture 3 of the gelation agent soluble in cold water and microorganism culture medium. Further, an absorbent fibrous sheet 4 is laid on the mixture 3. When the sample solution including microorganisms is poured onto the absorbent sheet 4, the solution is dispersed uniformly over the entire of the absorbent fibrous sheet 4 by the phenomenon of capillary attraction resulting from overlapped fibers. Subsequently, the mixture 3 of the gelation agent and culture medium coated on the plate 2 absorbs moisture and forms a gel. The fibers of the absorbent fibrous sheet 4 are buried and adhered into the mixture 3, thereby forming a gel medium for the culture of microorganisms.

3 Claims, 4 Drawing Sheets

APPARATUS FOR CULTURING MICROORGANISM

TECHNICAL FIELD

This invention relates to an apparatus for culturing microorganisms.

BACKGROUND ART

Conventionally, the mixing using a plate count method is carried out for measuring the number of microorganisms existing in food or others. Specifically, after introducing a specified amount of sample solution into a sterilized petri dish, an agar culture medium is poured into the petri dish. The agar culture medium is beforehand steam-sterilized under high pressure and retained at about 45° C. Immediately after being poured into the petri dish, the culture medium is sufficiently mixed with the sample solution. Subsequently, after the petri dish is left stationary and the culture medium completely solidifies, the culture is carried out in an incubator.

In the aforementioned conventional method, however, an autoclave or other special apparatus is required for heating, dissolving and steam-sterilizing under high pressure the agar culture medium. The petri dish, a flask for dissolving the agar culture medium and a number of other glass apparatuses are also required. Furthermore, to separate and cultivate microorganisms effectively, the sample solution has to be inoculated and mixed with the culture medium efficiently in a sterile manner and within a specified time period. For this purpose a laboratory should be installed especially for the microorganism test and a sufficiently trained technical expert should carry out the test. Therefore, it was difficult to carry out the microbiological quality test in general food processing plants.

To solve the aforementioned problem various simple culture media or simple test methods have been developed. For example, in a developed method, a specified amount of sample solution is permeated into the filter paper, which was impregnated with culture medium and was then dried (the trade name "Sankoritep" manufactured by Sun Kagaku Kabushiki Kaisha) so as to grow microorganisms. In this method, by impregnating the filter paper with the test solution, the culture medium is dissolved. The microorganisms in the test solution are nourished by the dissolved culture medium to grow.

In another developed method, the agar medium (for example, the trade name "Food Plate" manufactured by Nissui Seiyaku Kabushiki Kaisha) formed thin on the surface of a synthetic resin support member is soaked in the test solution for the culture of microorganisms. In this method, by soaking the agar medium in the sample solution once, the microorganisms in the test solution adhere to the surface of the agar medium. After the agar medium is drained, the culture is carried out.

In the method in which the filter paper impregnated with the culture medium is used, microorganisms often form unshapen colonies. Specifically, in this method, the test solution is held in the fibers of filter paper just by the phenomenon of capillary attraction. Motile microorganisms can freely move in the filter paper. Therefore, different from the agar media method in which microorganisms are firmly caught in the agar gel, microorganisms form the colonies spreaded in a wide area. It is also difficult to impregnate the entire filter paper uniformly with the sample solution. Consequently, it is difficult to exactly count the number of microorganisms because of the colonies overlapping one another on the filter paper or for other reasons.

In the method in which the thin formed agar medium is soaked in the test solution, the number of the microorganisms adhering to the surface of the agar medium does not exactly correspond to that of the microorganisms existing in the test solution. Therefore, we can just know the tendency to a large or small number of microorganisms.

Wherefore, an object of the invention is to provide an apparatus for the culture of microorganisms in which microorganisms are uniformly dispersed in the test solution and can form shapely colonies.

DISCLOSURE OF THE INVENTION

To attain the aforementioned object, the invention provides an apparatus for the culture of microorganisms characterized in that at least a part of the surface of a waterproof plate is coated with the mixture of a gelation agent soluble in cold water and a microorganism culture medium and that an absorbent fibrous sheet is laid over at least a part of the surface of the coating.

In the invention having the aforementioned structure the surface of the waterproof plate is coated with the mixture of the gelation agent soluble in cold water and the microorganism culture medium. By dropping a specified amount of sample solution onto the absorbent fibrous sheet laid over the surface of the coating, with a pipette or other apparatus, the sample solution is diffused in the entire absorbent sheet in the phenomenon of capillary attraction caused by the overlapping of the fibers forming the absorbent fibrous sheet. At the same time the gelation agent soluble in cold water coating the surface of the plate absorbs the test solution, swells and gels, thereby dissolving the microorganism culture medium. The fibers of the absorbent fibrous sheet are buried in the gel or adhered to the gel. Thus, the microorganisms in the test solution are captured in the gel and are inhibited from moving freely. Consequently, the microorganisms are uniformly dispersed and the countable microorganism colonies are formed.

BRIEF EXPLANATION OF DRAWING FIGURES

BEST MODE FOR CARRYING OUT THE INVENTION

Figure 1:
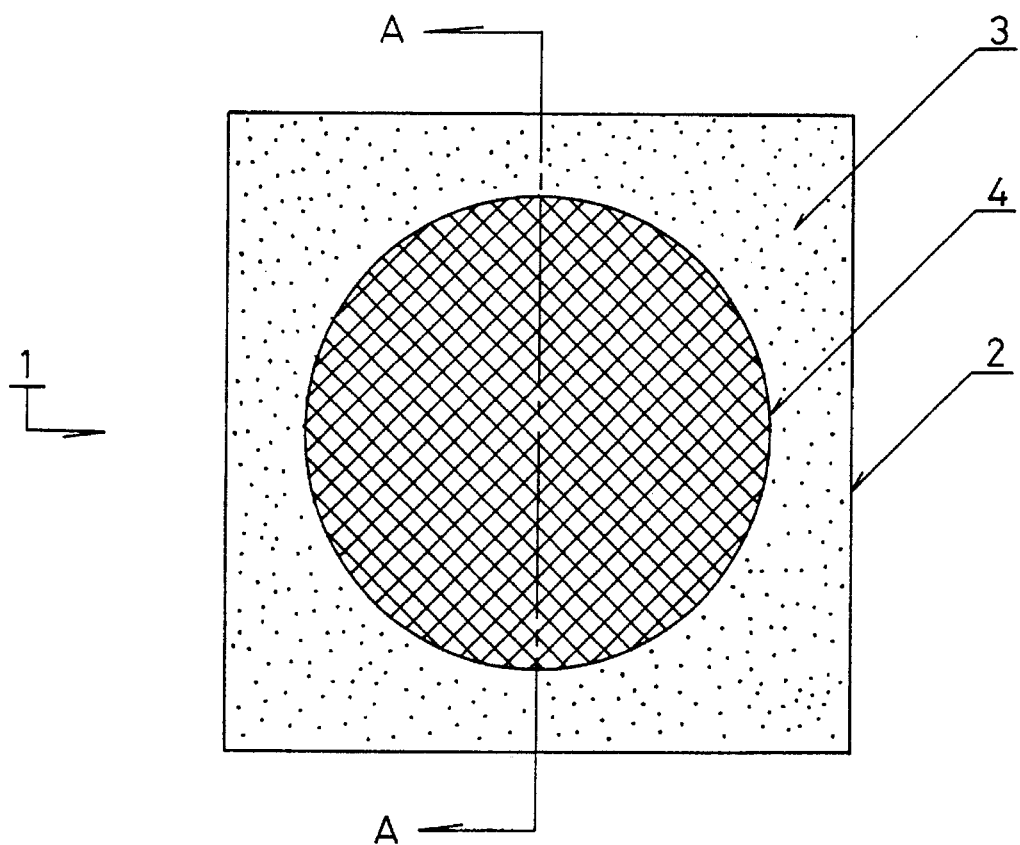
FIG. 1 is a plan view showing an apparatus for the culture of microorganisms embodying the invention.

The embodiment of the invention is now explained referring to the drawing figures.

Figure 2:
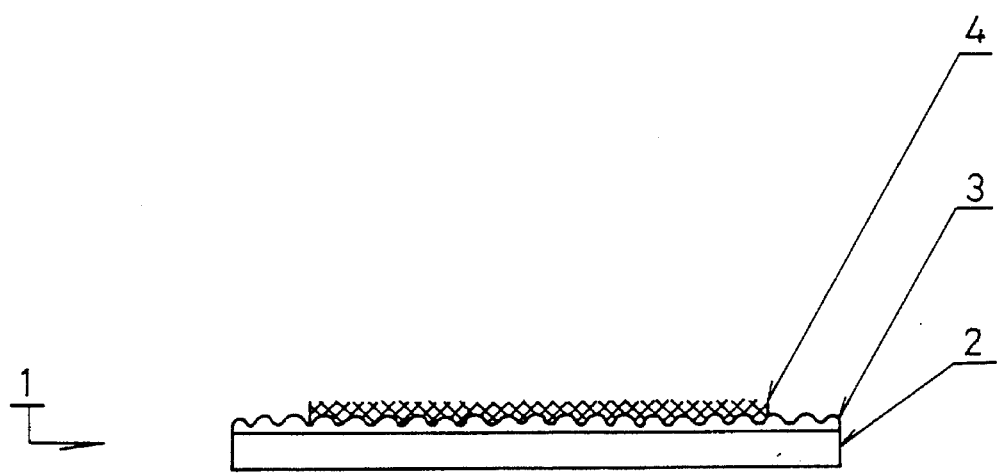
FIG. 2 is a cross-sectional view of FIG. 1.

FIG. 1 is a plan view of an apparatus for the culture of microorganisms embodying the invention, and FIG. 2 is a cross-sectional view taken along the line A—A of the apparatus for the culture of microorganisms shown in FIG. 1. As shown in the figures, the apparatus for the culture of microorganisms has a square waterproof plate 2 whose surface is coated with a mixture 3 of gelation agent soluble in cold water and microorganism culture medium. The surface of the coating is provided with a circular absorbent fibrous sheet.

The plate 2 is formed of white polystyrene resin, and matte finish is applied to the surface of the plate 2 such that the mixture of the gelation agent soluble in cold water and the microorganism culture medium can be easily adhered to the surface of the plate 2. The configuration of the plate 2 is not limited to a square. The plate 2 can be formed into any other configuration that can be laminated completely covering the absorbent fibrous sheet. The material of the plate 2 is not limited to polystyrene resin, and can be any other waterproof material. The finish of the plate 2 is not limited to matte finish.

The surface of the plate 2 is coated with the mixture 3 of the gelation agent soluble in cold water and the microorganism culture medium. Carageenan is used as the gelation agent soluble in cold water. The amount of the gelation agent is adjusted such that the sufficient gel strength can be obtained when a specified amount of sample solution is diffused in a predetermined area and the gelation agent soluble in cold water is hydrated. As the microorganism culture medium, peptone, yeast extract and glucose are used. The amount of the microorganism culture medium is adjusted, such that peptone, yeast extract and glucose amount to 0.5%, 0.25% and 0.1% by weight relative to the test solution, respectively, and so-called standard culture medium is formed, when a specified amount of test solution is diffused in a predetermined area, thereby dissolving the microorganism culture medium. The mixture of the gelation agent soluble in cold water and the culture medium is kneaded in a mud condition in the 80% ethanol solution in which polyvinyl pyrolidone as a fixing agent is already dissolved. After the kneaded mixture is applied uniformly to the plate 2, the plate 2 is dried, thereby forming the coating on the surface of the plate 2.

The gelation agent soluble in cold water is not limited to carageenan. Guar gum, xanthum gum, carboxy-methyl cellulose, polyvinyl alcohol or any other gelation agent can be used so far as sufficient gel strength can be obtained. The microorganism culture medium can include various components according to the kind of microorganism to be cultivated. The selective inhibitor for microorganisms, an indicator, a coloring element or other can be included in the medium. Since the plate 2 is coated with the mixture 3 of the gel soluble in cold water and the culture medium, the fixing agent is not necessarily needed.

As the absorbent fibrous sheet 4 laid on the surface of the plate 2 coated with the mixture 3 of the gelation agent soluble in cold water and the microorganism medium, nonwoven fabric of rayon is used. The area of the sheet 4 is adjusted, such that when a specified amount of test solution is poured, the entire nonwoven fabric is impregnated uniformly and sufficiently with the test solution. The absorbent fibrous sheet is not limited to the nonwoven fabric of rayon. Handmade paper, woven fabric, nonwoven fabric or any other material of hydrophilic fibers can be used. The thickness of the sheet 4 is not especially limited. However, when the thickness is between about 0.1 mm and about 0.2 mm, the sheet 4 absorbing the test solution becomes transparent or translucent. Therefore, the colonies of microorganisms can be easily observed.

In the culture apparatus 1 having the aforementioned structure according to the embodiment, microorganisms can be cultivated as follows. Specifically, a predetermined amount of test solution including microorganisms (for example, the homogenate resulting from the homogenization of food sample and sterile physiological salt solution) is first poured onto the absorbent fibrous sheet 4 by using a sterilized pipette. The test solution is uniformly diffused in the entire absorbent fibrous sheet 4 in the phenomenon of capillary attraction caused by the overlapping of fibers. Subsequently, the mixture 3 of the gelation agent soluble in cold water and the microorganism culture medium absorbs the test solution and forms a gel. The fibers of the absorbent fibrous sheet 4 are buried in the gel or adhered to the gel, thereby forming the medium. Therefore, the microorganisms in the test solution are captured in the gel. The microorganism culture apparatus 1 is then housed in a suitable sealed container to avoid contamination and drying. Microorganisms are cultivated at a specified temperature.

In the embodiment, the medium can be formed just by pouring the test solution onto the absorbent fibrous sheet 4. Consequently, a special laboratory or an expert is not necessary for the test of microorganisms. Anyone can easily carry out the microorganism test anywhere.

Furthermore, in the embodiment, the test solution is diffused uniformly in the whole of the absorbent fibrous sheet 4 in the capillary phenomenon. The microorganisms in the test solution are captured in the gel and are prohibited from moving freely. No colonies of microorganisms overlap one another. Shapely colonies of microorganisms can be formed. Consequently, the number of microorganisms can be exactly counted.

Figure 3:
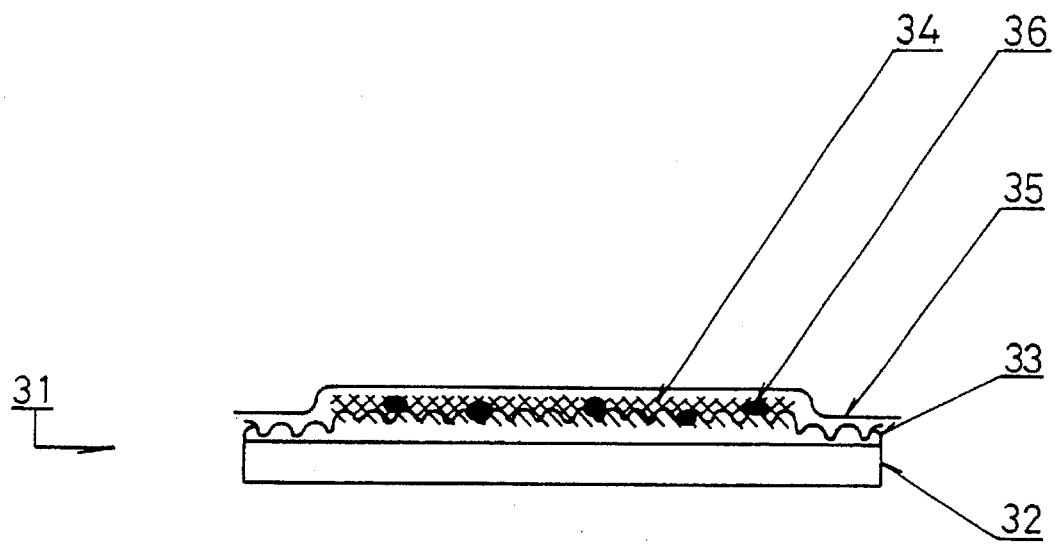
FIG. 3 is a cross-sectional view showing the status (the time of the culture of microorganisms) in which a cover film is laid over the apparatus for the culture of microorganisms embodying the invention.

In the embodiment after the test solution is poured and the gel medium is formed, the microorganism culture apparatus 1 is contained in the sealed container for the sake of the prevention of contamination and dry, for the culture of microorganisms. Alternatively, a cover film can be laid over the apparatus 1, such that the apparatus 1 is prevented from being contaminated and dried. As shown in FIG. 3, a cover film 35 is laid over an apparatus 31 for the culture of microorganisms. The cover film 35 is transparent, is impermeable to moisture and microorganisms, and has a size enough to completely cover an absorbent fibrous sheet 34. The cover film 35 is lifted up, the absorbent fibrous sheet 34 is exposed, and the test solution is poured onto the absorbent fibrous sheet 34. Subsequently, the cover film is returned to the original position, and comes in close contact with the absorbent fibrous sheet having absorbed the test solution. The culture apparatus 31 can thus be prevented from being contaminated and dried. Microorganisms can be cultivated without housing the microorganism culture apparatus 31 in the sealed container.

Figure 4:
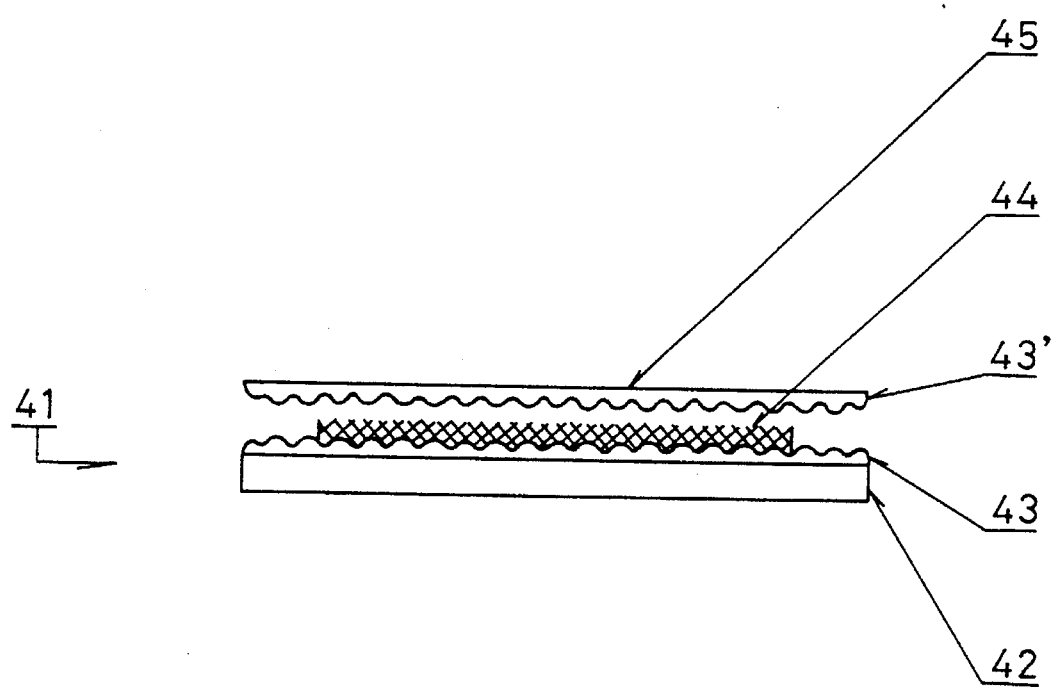
FIG. 4 is a cross-sectional view showing that the cover film coated with the mixture of a gelation agent soluble in cold water and a microorganism culture medium is laid over the apparatus for the culture of microorganisms embodying the invention.

As shown in FIG. 4, for the purpose of the prevention of contamination and drying, the mixture 43' of the gelation agent soluble in cold water and the microorganism culture medium is coated on the cover film surface in contact with the gel medium, in the same way as the coating 43 on the surface of a plate 42. When the test solution is poured and the cover film is put in close contact with the test solution, the coating 43' on the surface of the cover film absorbs the test solution and forms a gel. The gel on the surface of the plate is combined with the gel on the surface of the cover film through the absorbent fibrous sheet. The plate 42, the absorbent fibrous sheet 44 and the cover film 45 adhere firmly to one another. Therefore, the stability of the gel portions and the formation of the microorganism colonies can be enhanced. Either one of the respective surface coatings of the plate 42 and the cover film 45 can be formed only by the gelation agent soluble in cold water.

EXPERIMENTAL EXAMPLES

The experimental examples are hereinafter described for proving the effectiveness of the above embodiments. Experiments were carried out as follows. First, for the apparatus 31 for the culture of microorganisms, a square plate having each 8.0 cm long side and a thickness of 1.0 mm was prepared as a plate 32. Nonwoven rayon fabric having a diameter of 6.0 cm was prepared as the absorbent fibrous sheet 34 (25 g/square meter at standard, about 0.2 mm thick). As the cover film 35 a polyethylene film having a thickness of 0.08 mm was prepared. Subsequently, 1 ml of test solution was poured to the apparatus for the culture of microorganisms. The test solution was prepared by homogenizing raw squid with sterile physiological salt solution to form a homogenate and then diluting the homogenate appropriately with sterile physiological salt solution. The gel medium was formed by the aforementioned steps.

On the other hand, a reference example was prepared. Immediately after 1 ml of the aforementioned test solution was poured to the petri dish having an inner diameter of 6 cm, about 5 ml of standard agar medium maintained at about 45° C. was poured to the petri dish so as to mix with the test solution. Subsequently, the petri dish was laid still and cooled, thereby solidifying the medium.

Subsequently, the respective media as the embodiment and the reference example were cultivated at 35° C. for 48 hours. The number of developed colonies was counted. Such experiment was repeated 10 times for each medium. As a result, the average number of colonies per 1 ml of test solution was 167 for the embodiment and 173 for the reference example. Only slight difference in number was seen between the embodiment and the reference example. The condition of dispersion of microorganism colonies in the embodiment is the same as that in the reference example. The microorganisms are prevented from being captured in the nonwoven fabric and being concentrated to some part. The configuration of the colonies is shaped.

From the aforementioned experimental results, it was found that the operation of the apparatus 31 for the culture of microorganisms in the embodiment was made remarkably simpler as compared with that of the conventional apparatus. Therefore, it was proved that by using the apparatus 31 for the culture of microorganisms, microorganisms can be cultivated and examined without installing a special laboratory for the microorganism test or mastering the expertise.

INDUSTRIAL APPLICABILITY

As aforementioned, according to the present invention, the test solution poured onto the absorbent fibrous sheet was uniformly dispersed over the whole of absorbent fibrous sheet by the phenomenon of capillary attraction caused by the overlapped fibers forming the sheet. Therefore, the pouring and dispersing of the test solution requires no skill. The gelation agent soluble in cold water absorbs the test solution, forms a gel and captures microorganisms. Since the microorganisms are prohibited from moving :freely, the shapely microorganism colonies are formed. Therefore, no microorganism colonies overlap one another. The number of the colonies can be easily counted.

When the apparatus for the culture of microorganisms according to the present invention is operated, dissolution by heating, sterilization under high pressures and other special method are not required for preparing media. Consequently, even a nonexpert can easily carry out the microorganism test in a not-equipped laboratory. At the same time, since the sheet is dry before the time of use, the device can be stored for a long time and can be prepared for emergency use for examination.

What is claimed is:

1. An apparatus for the culture of microorganisms characterized in that at least a part of the surface of a waterproof plate is coated with the mixture of a gelation agent soluble in cold water and a microorganism culture medium and that an absorbent fibrous sheet is laid over at least a part of the surface of said coating.

2. An apparatus for the culture of microorganisms according to claim 1 in which a transparent cover film impermeable to moisture and microorganisms having a size sufficiently large to completely cover said absorbent fibrous sheet is laid to completely cover said absorbent fibrous sheet.

3. An apparatus for the culture of microorganisms according to claim 2 in which the surface in contact with said absorbent fibrous sheet, of said cover film is coated with the mixture of a gelation agent soluble in cold water and a microorganism culture medium or with the gelation agent soluble in cold water.

* * * * *